United States Patent
Kim

(10) Patent No.: US 10,278,659 B2
(45) Date of Patent: May 7, 2019

(54) C-ARM HEAD COVER

(71) Applicant: KYUNGPOOK NATIONAL UNIVERSITY INDUSTRY—ACADEMIC COOPERATION FOUNDATION, Daegu (KR)

(72) Inventor: Kyoung Tae Kim, Daegu (KR)

(73) Assignee: Kyungpook National University Industry—Academic Cooperation Foundation, Daegu (KR)

( * ) Notice: Subject to any disclaimer, the term of this patent is extended or adjusted under 35 U.S.C. 154(b) by 209 days.

(21) Appl. No.: 15/519,312

(22) PCT Filed: Oct. 15, 2015

(86) PCT No.: PCT/KR2015/010930
§ 371 (c)(1),
(2) Date: Apr. 14, 2017

(87) PCT Pub. No.: WO2016/060505
PCT Pub. Date: Apr. 21, 2016

(65) Prior Publication Data
US 2017/0238888 A1    Aug. 24, 2017

(30) Foreign Application Priority Data
Oct. 15, 2014    (KR) ........................ 10-2014-0138897

(51) Int. Cl.
*A61B 6/10*    (2006.01)
*G21F 1/08*    (2006.01)
(Continued)

(52) U.S. Cl.
CPC .......... *A61B 6/4423* (2013.01); *A61B 6/4441* (2013.01); *A61B 46/20* (2016.02); *A61B 6/4405* (2013.01); *A61B 2046/205* (2016.02)

(58) Field of Classification Search
CPC ......... A61B 46/40; A61B 50/00; A61B 90/00; A61B 6/10
See application file for complete search history.

(56) References Cited

U.S. PATENT DOCUMENTS 9,655,571 B2 *  5/2017  Hunt ................... A61B 6/0407
2009/0255541 A1  10/2009  Kaska
(Continued)

FOREIGN PATENT DOCUMENTS

JP    H07-148147 A    6/1995
JP    2005-007064 A   1/2005
(Continued)

*Primary Examiner* — Don K Wong
(74) *Attorney, Agent, or Firm* — Novick, Kim & Lee, PLLC; Sang Ho Lee

(57) ABSTRACT

The present invention relates to a C-arm head cover. The C-arm head cover according to the present invention comprises: a fixed unit which includes a fixing means, and is capable of being fixed to a predetermined object; a first cover which extends from the fixed unit, and has a foldable structure; and a second cover which extends from the first cover, and is bent downward, wherein when the C-arm head rotates 180 degrees from an upright position around a C-arm table for supporting a person to be processed with radiography, the foldable structure of the first cover is unfolded, and then only the first cover or both the first cover and the second cover covers the C-arm head.

20 Claims, 10 Drawing Sheets

(51) Int. Cl.
*A61B 6/00* (2006.01)
*A61B 46/20* (2016.01)

(56) References Cited

U.S. PATENT DOCUMENTS

| | | | |
|---|---|---|---|
| 2010/0275929 A1 | 11/2010 | Kaska | |
| 2011/0041995 A1 | 2/2011 | Adams | |
| 2015/0320370 A1* | 11/2015 | Bouvier | A61B 6/035 378/189 |
| 2016/0038103 A1* | 2/2016 | Cadwalader | A61B 6/107 250/515.1 |

FOREIGN PATENT DOCUMENTS

| | | |
|---|---|---|
| JP | 2006-511285 A | 4/2006 |
| KR | 2003-0045737 A | 6/2003 |
| KR | 10-1218378 B1 | 1/2013 |
| KR | 10-1415600 B1 | 8/2014 |
| WO | 1997017035 A1 | 5/1997 |

\* cited by examiner

C-ARM HEAD COVER

TECHNICAL FIELD

The present invention relates to a C-arm head cover used in a radiographic imaging device, and more particularly, to a C-arm head cover capable of preventing frequent replacements of a sterile cloth by adjusting the shape of the C-arm head cover according to a position of the C-arm head cover.

BACKGROUND ART

Radiographic diagnosis is for realizing a form of an internal organ and the like into an image using x-rays to recognize the form. That is, radiographic diagnosis refers to recognizing a form of a disease or a change thereof from an image captured using x-rays.

The radiographic imaging technology is used as a very important technology in an orthopedic or neurosurgical operation. Specifically, the radiographic imaging technology is mainly used as a method of recognizing an accurate site when inserting a screw into fractured bones or bones, and is also used in checking an operation target site. However, in order to obtain accurate images, it is important to capture various angles, and a C-arm is a typical instrument which is mostly used for this.

A C-arm structure is a structure in which an x-ray source and an x-ray detector are mounted to face each other at both ends of a C-shaped gantry having a circular shape with one side opened and the x-ray source and the x-ray detector can rotate about a patient by the C-arm gantry rotating about a pivot axis mounted at a center of the C-shape (refer to Korean Patent Application No. 10-2003-0029847).

In an actual operation, a C-arm gantry rotates about a patient to obtain an accurate and appropriate image, and in this process, the C-arm gantry descends to a lower portion of the table on which a patient is placed. Here, contamination of the C-arm gantry may occur, and a sterile cloth and the like set for the patient may be contaminated when the C-arm gantry is moved to an upper portion of the table afterwards. To perform imaging again, the contaminated head portion should be covered again with a new sterile cloth. Here, imaging is not performed smoothly because a problem in that a sterile cloth needs to be frequently replaced occurs, and sterile cloths are wasted.

DISCLOSURE

Technical Problem

In order to solve the above problem, the need for a C-arm head cover which covers the contaminated C-arm head and enables radiographic imaging to be performed several times by setting a sterile cloth for one time is coming into the limelight.

It is an aspect of the present invention to provide a C-arm head cover capable of preventing frequent replacements of a sterile cloth by adjusting the shape of the C-arm head cover according to a position of the C-arm head cover.

Aspects of the present invention are not limited to those mentioned above, and other unmentioned aspects thereof are to be clearly understood by one of ordinary skill in the art from the description below.

Technical Solution

According to an embodiment of the present invention for achieving the above aspects, a C-arm head cover is a C-arm head cover which constitutes a radiographic imaging device. The C-arm head cover includes a fixing part having a fixer to be able to be fixed to a predetermined object, a first cover extending from the fixing part and having a folding structure, and a second cover extending from the first cover and hanging downward. When the C-arm head passes a lower portion of a C-arm table, which supports a target to be radiographically imaged, and moves to an upper portion, the folding structure of the first cover is unfolded, and the first cover or the first cover and the second cover may cover the C-arm head.

According to another embodiment of the present invention for achieving the above aspects, a C-arm head cover is a C-arm head cover which constitutes a radiographic imaging device. The C-arm head cover includes a first cover having a folding structure and a second cover extending from the first cover and hanging downward. A fixing part may be formed at an outer surface of an outer boundary portion disposed at an opposite side of the second cover of portions forming the folding structure of the first cover, the fixing part may have a fixer so that the first cover can be fixed to a predetermined object, and, when the C-arm head passes a lower portion of a C-arm table, which supports a target to be radiographically imaged, and moves to an upper portion, the folding structure of the first cover may be unfolded, and the first cover or the first cover and the second cover may cover the C-arm head.

Advantageous Effects

According to the present invention, a C-arm head cover capable of preventing frequent replacements of a sterile cloth by adjusting the shape of the C-arm head cover according to a position of the C-arm head cover can be provided.

DESCRIPTION OF REFERENCE NUMERALS

Figure 1:
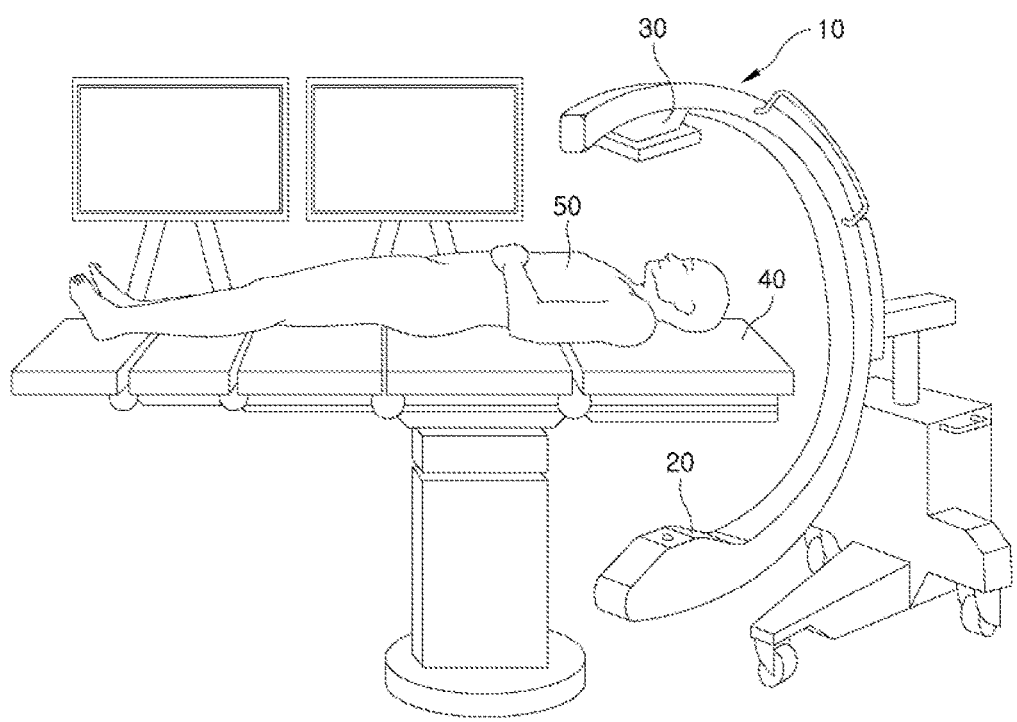
FIG. 1 is a schematic view of a C-arm which constitutes a radiographic imaging device.

10: C-arm
20, 30: C-arm head
40: C-arm table
50: Patient
73: Storage space
75: Portion fixed to sterile cloth 80, 150: Fixing part
81, 83, 115, 120, 165, 168: Folding part
85, 110, 135, 160: First cover
87, 125, 137, 163: Attaching portion
90, 140: Second cover
93, 145: Weight member
100, 130: C-arm head cover
127: Form keeper

MODES OF THE INVENTION

Advantages and features of the present invention and a method of achieving the same should become clear with embodiments described in detail below with reference to the accompanying drawings. However, the present invention is not limited to embodiments disclosed below and is realized in various other forms. The present embodiments make the disclosure of the present invention complete and are provided to completely inform one of ordinary skill in the art to which the present invention pertains of the scope of the invention. The present invention is defined only by the scope of the claims. Like reference numerals refer to like elements throughout.

Terms used herein are for describing the embodiments and are not intended to limit the present invention. In the specification, a singular expression includes a plural expression unless the context clearly indicates otherwise. "Comprises" and/or "comprising" used herein do not preclude the existence or the possibility of adding one or more elements, steps, and operations other than those mentioned.

Figure 2:
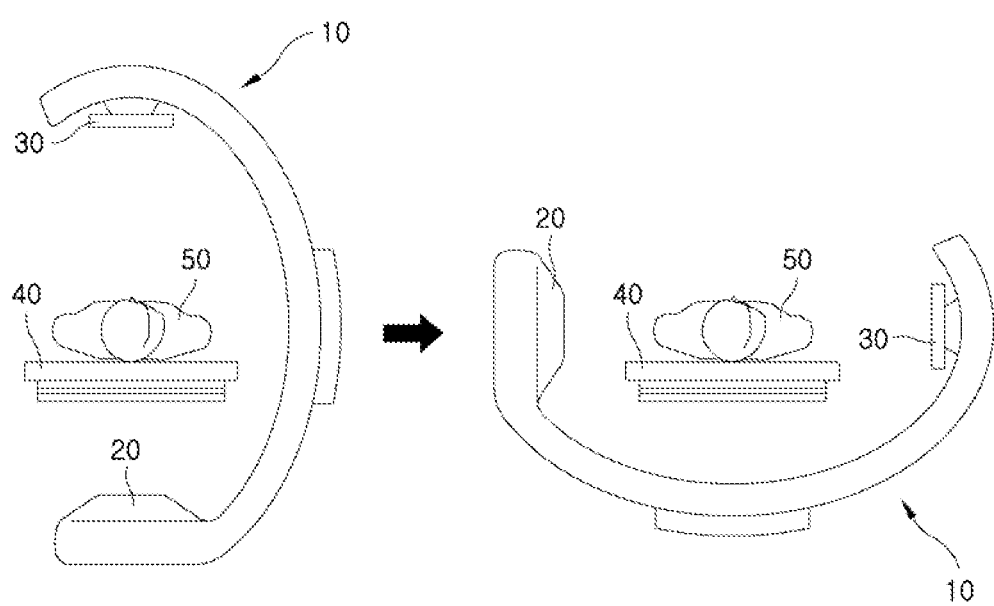
FIG. 2 is a schematic view illustrating a moving shape of the C-arm.

A C-arm which constitutes a radiographic imaging device will be described with reference to FIGS. 1 and 2. FIG. 1 is a schematic view of a C-arm constituting a radiographic imaging device. FIG. 2 is a schematic view illustrating a moving shape of the C-arm.

A medical radiographic imaging device may have a C-shaped C-arm 10 configured to connect an x-ray generator which generates x-rays and an x-ray detector which detects x-rays generated by the x-ray generator, and the x-ray generator and the x-ray detector constitute C-arm heads 20 and 30. Because the C-arm 10 is connected to a rotating shaft of a rotary block of a main body connected to a monitor, the medical radiographic imaging device irradiates a test object such as a patient or an animal body with x-rays by the x-ray generator in a state in which a rotating shaft of the C-arm 10 may be constantly rotated by any angle from a reference angle, detects x-rays that have passed through the test object by the x-ray detector, processes the detected x-rays into an image in the main body, and then displays the processed image on the monitor.

Also, the medical radiographic imaging device has a C-arm table 40 configured to have a patient placed thereon. The C-arm table 40 is a table which may be used in a diagnostic device such as the medical radiographic imaging device, and may be provided so that the C-arm head 20 may pass a lower end of the table and rotate.

Generally, when a doctor examines or treats a patient 50 placed on the C-arm table 40, a sterile cloth is placed on an upper part of the patient, and the C-arm head 20 is placed at the lower end of the table to capture a front image of the patient 50 in a radiographic imaging process. Here, the C-arm head 20 may be contaminated, and afterward, the sterile cloth placed on the patient 50 may be contaminated in a process in which the contaminated C-arm head 20 passes the lower end, rotates, and moves to an upper portion of the table to capture a side image of the patient 50.

Consequently, an inconvenience of having to replace a sterile cloth several times during radiographic imaging is generated, and this has a negative effect on the cleanliness of therapeutic and treatment setting as a whole.

The C-arm head cover according to an embodiment of the present invention has been devised to solve the above problem. Hereinafter, this will be described in detail.

Figure 3:
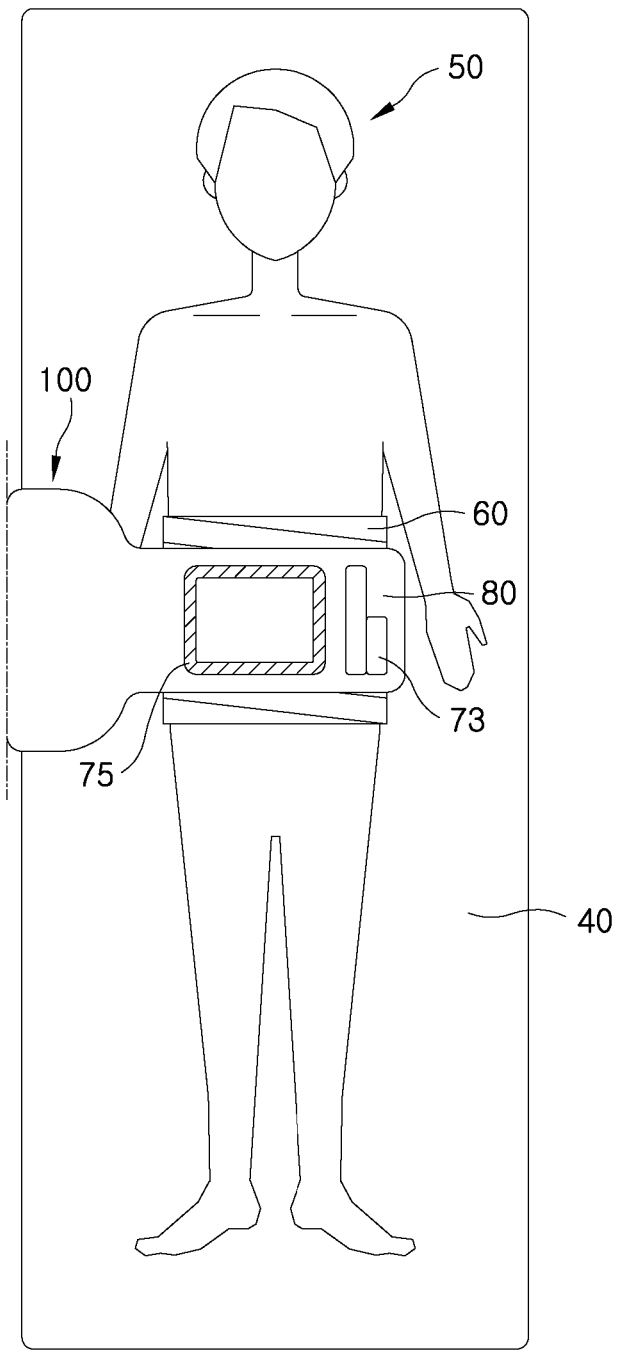
FIG. 3 is a view illustrating a usage form of the C-arm head cover according to an embodiment of the present invention.
Figure 4:
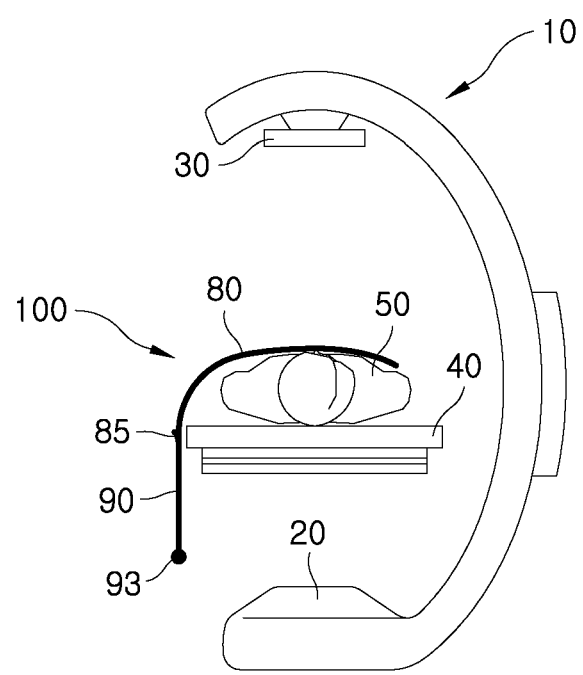
FIGS. 4 to 6 are views illustrating a process in which the C-arm head cover according to an embodiment of the present invention is unfolded.
Figure 5:
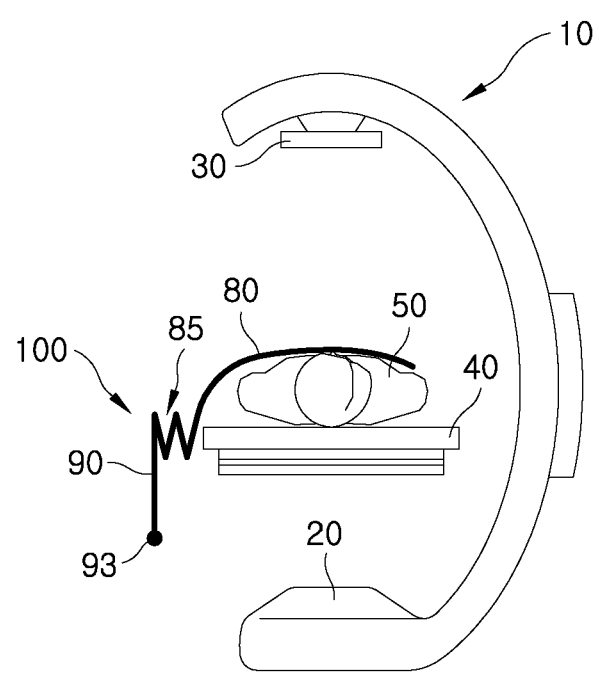
Figure 6:
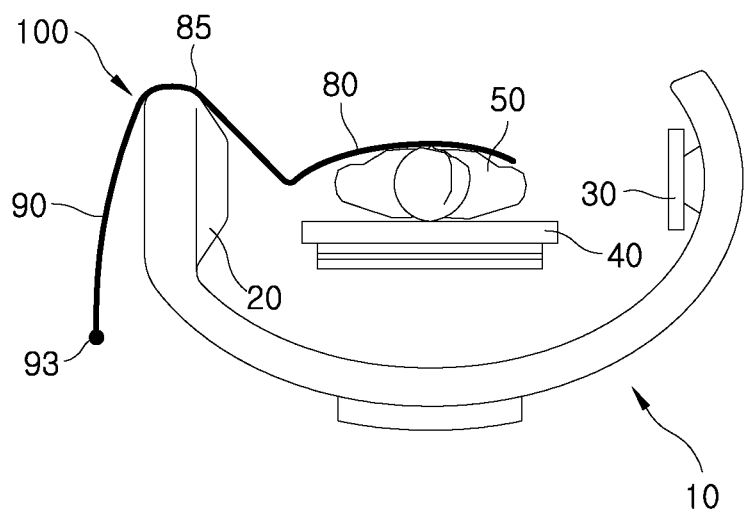
Figure 7:
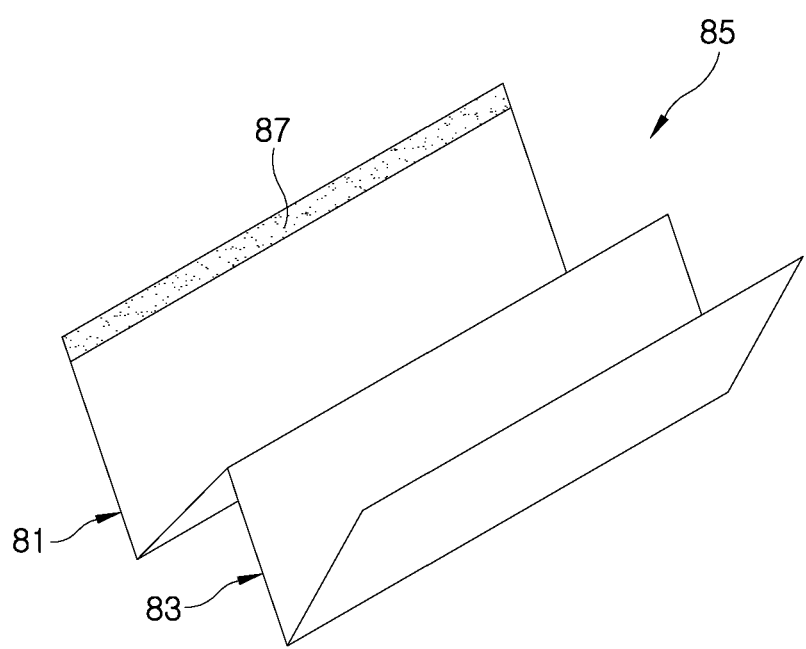
FIG. 7 is a view illustrating a first cover part of the C-arm head cover according to an embodiment of the present invention.

The C-arm head cover according to an embodiment of the present invention will be described with reference to FIGS. 3 to 7. FIG. 3 is a view illustrating a usage form of the C-arm head cover according to an embodiment of the present invention. FIGS. 4 to 6 are views illustrating a process in which the C-arm head cover according to an embodiment of the present invention is unfolded. FIG. 7 is a view illustrating a first cover part of the C-arm head cover according to an embodiment of the present invention.

A C-arm head cover 100 according to an embodiment of the present invention may include a fixing part 80, a first cover 85, and a second cover 90.

The fixing part 80 may have a fixer and be fixed to a predetermined object, and thus enables the C-arm head cover 100 to be fixed to the predetermined object. For example, the fixing part 80 may be fixed to a sterile cloth 60 of a patient by an adhesive which is a fixer, or an adhesive may also be applied on the sterile cloth 60 and the fixing part 80 may be fixed to the sterile cloth.

Further, a storage space 73 may be formed in a remaining portion of the fixing part 80 except a portion 75 of the fixing part 80 fixed to the sterile cloth. Because a doctor may store treatment tools and the like in the storage space 73, the doctor may more easily perform treatments.

The first cover 85 is a portion formed by extending from the fixing part 80 and forms a folding structure. Although the first cover 85 does not cover the C-arm head 20 when the folding structure is folded, the first cover 85 may serve as a cover for covering the C-arm head 20 when the folding structure is unfolded.

The first cover 85 serving as the cover will be described in more detail. When the radiographic imaging device captures a front image of the patient 50, the C-arm head 20 is placed at a lower portion of the C-arm table 40, and the first cover 85 is folded because contamination of the sterile cloth 60 due to the C-arm head 20 does not have to be taken into consideration in this state. The first cover 85 is folded also for securing a doctor's examination space.

On the other hand, when the radiographic imaging device captures a side image of the patient 50, the C-arm head 20 which was placed at the lower portion of the C-arm table 40 is contaminated, the folding structure of the first cover 85 is unfolded in a process in which the C-arm head 20 is rotated and moved upward, and the unfolded first cover 85 covers the C-arm head 20 to protect the sterile cloth 60 from the contaminated C-arm head 20.

Consequently, because the sterile cloth 60 does not have to be replaced even when the C-arm head 20 which was placed at the lower portion of the table is moved upward to capture a side image of the patient 50, treatments or therapies can be efficiently and promptly performed.

The folding structure of the first cover 85 will be described in detail. The folding structure may include one or more V-shaped folding parts, and adjacent V-shaped folding parts are connected to each other to form the folding structure. Related to this, referring to FIG. 7, the folding structure may include two V-shaped folding parts 81 and 83, the two V-shaped folding parts 81 and 83 may be connected to each other and form a folding structure having a W-shape as a whole, and a central protruding portion, which is a portion of the W-shaped folding structure in which the two V-shaped folding parts are connected to each other, may have a height smaller than those of both end portions of the W-shape.

In this case, an attaching portion 87 may be formed at upper ends of inner surfaces of both end portions, which are outer boundary portions of the W-shape, and only the upper ends of the inner surfaces of the both end portions of the W-shape may be attached to each other when the folding structure is folded. A Velcro tape may be formed at the attaching portion 87, a male loop of the Velcro tape may be formed at one end portion of the both end portions of the W-shape, and a female loop of the Velcro tape may be formed at the remaining end portion.

Although mentioned above, the number of the V-shaped folding parts forming the folding structure may be one or three or more unlike in FIG. 7. When the folding structure has three or more V-shaped folding parts, of portions forming the folding parts disposed at both ends among the three or more folding parts, attaching portions may be formed at inner surfaces of outer portions based on the folding structure, and the folding structure may be folded as the attaching portions are attached to each other.

The second cover 90 is a portion formed by extending from the first cover 85, and may have a form hanging downward and serve as a cover for covering the C-arm head 20.

The second cover 90 serving as the cover will be described in more detail. When the radiographic imaging device captures a front image of the patient 50, the C-arm head 20 is placed at the lower portion of the C-arm table 40, and in this case, the second cover 90 may have a form hanging downward. On the other hand, when the radiographic imaging device captures a side image of the patient 50, the C-arm head 20 which was placed at the lower portion of the C-arm table 40 is contaminated, and, in a process in which the C-arm head 20 is rotated and moved upward, the second cover 90 covers the C-arm head 20 to protect the sterile cloth 60 from the contaminated C-arm head 20.

Consequently, because the sterile cloth 60 does not have to be replaced even when the C-arm head 20 which was placed at the lower portion of the table is moved upward to capture a side image of the patient 50, treatments or therapies can be efficiently and promptly performed.

Meanwhile, the C-arm head cover 100 may be formed of any material through which radiation radiated from the medical radiographic imaging device can pass and may also be formed of a transparent material.

Further, the C-arm head cover 100 according to an embodiment of the present invention may further include a weight member 93 in addition to the above-mentioned fixing part 80, first cover 85, and second cover 90.

The weight member 93 may be attached to the second cover 90 and serve to cause the second cover 90 to be flatly hung downward. In this way, by using the weight member 93 to pull the second cover 90 downward, the second cover 90 is prevented from being placed in a movement path of a doctor who treats the patient 50, and the doctor may easily examine the patient 50 on the C-arm table 40.

Figure 8:
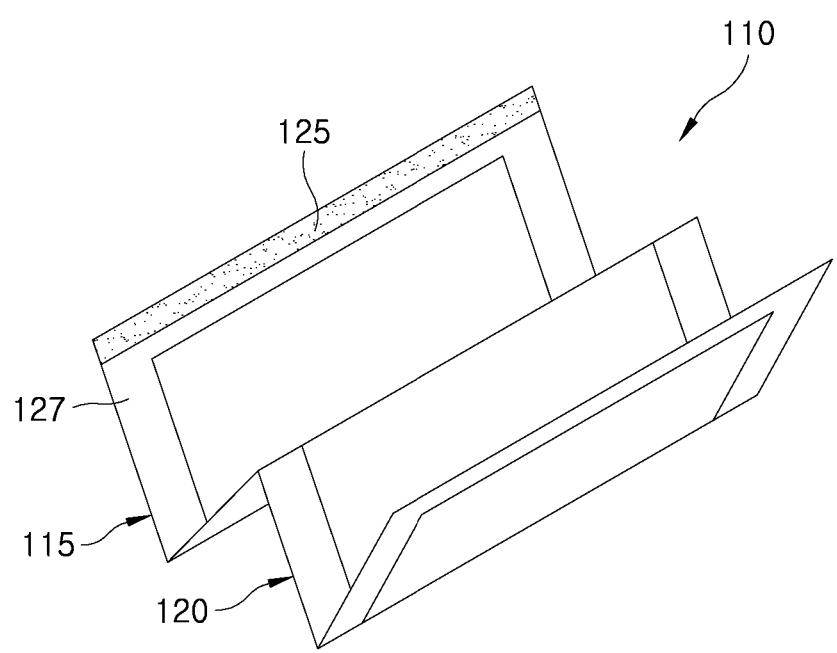
FIG. 8 is a view illustrating a first cover part of a C-arm head cover according to another embodiment of the present invention.

Hereinafter, a C-arm head cover according to another embodiment of the present invention will be described with reference to FIG. 8. FIG. 8 is a view illustrating a first cover part of the C-arm head cover according to another embodiment of the present invention.

Referring to FIG. 8, the C-arm head cover according to another embodiment of the present invention is different from the C-arm head cover 100 according to the above-mentioned embodiment of the present invention in terms of a first cover. Specifically, a form keeper 127 may be added to a first cover 110 of the C-arm head cover according to another embodiment of the present invention. The form keeper 127 may be formed along an outer boundary of the first cover 110. The form keeper 127 may include an interlining cloth, a finishing material, and a durable sheet. The interlining cloth, the finishing material, and the durable sheet may be attached to the first cover 110 along the outer boundary of the first cover 110.

In this way, by the form keeper 127 being added to the first cover 110, a weight may be assigned to the first cover 110 and a form thereof may be kept. Consequently, a folding structure of the first cover 110 can be easily folded or unfolded, and a folded state or an unfolded state of the folding structure can be maintained continuously.

Also, after the form keeper 127 is added along the outer boundary of the first cover 110, an attaching portion 125 may be formed on the form keeper 127. Specifically, the attaching portion 125 may be formed at a portion of the form keeper 127 added at upper ends of inner surfaces of both end portions of a W-shape. Because a portion of the W-shaped folding structure at which two V-shaped folding parts 115 and 120 are connected to each other may have a height smaller than those of the both ends of the W-shape, only the attaching portions at the both ends may be attached to each other and enable the first cover 110 to be folded.

Hereinafter, a C-arm head cover according to still another embodiment of the present invention will be described. The C-arm head cover according to still another embodiment of the present invention is different from the above mentioned C-arm head covers according to the embodiment and another embodiment of the present invention in terms of an attaching portion formed at a folding part of a folding structure.

Specifically, although a Velcro tape is used as an attaching portion in the above-mentioned C-arm head cover according to the present invention, the C-arm head cover according to still another embodiment of the present invention may have a snap button formed at an attaching portion and fold or unfold a folding structure by snap buttons.

In this way, because an adhesive force is not used for attaching when a snap button is used as an attaching portion, replacement due to a decrease of an adhesive force does not have to be taken into consideration, and thus the C-arm head cover can be used for a long period.

Figure 9:
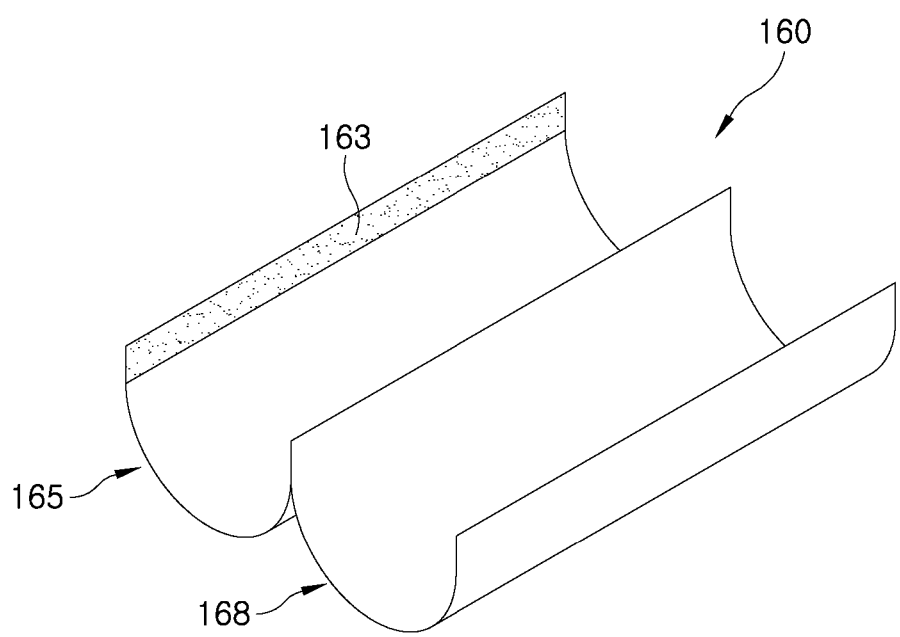
FIG. 9 is a view illustrating a C-arm head cover according to still another embodiment of the present invention.

Hereinafter, a C-arm head cover according to still another embodiment of the present invention will be described with reference to FIG. 9. FIG. 9 is a view illustrating a C-arm head cover according to still another embodiment of the present invention.

Referring to FIG. 9, the C-arm head cover according to still another embodiment of the present invention is different from the above-mentioned C-arm head cover according to the present invention in terms of a form of a folding structure of a first cover. Specifically, a folding structure of the C-arm head cover according to still another embodiment of the present invention includes a U-shaped folding part instead of a V-shaped folding part.

A folding structure of a first cover 160 includes two U-shaped folding parts 165 and 168, the two U-shaped folding parts 165 and 168 may be connected to each other, and a central protruding portion, which is a portion of the folding structure in which the two U-shaped folding parts are connected to each other, may have a height smaller than those of both end portions of the folding structure.

In this case, an attaching portion 163 may be formed at upper ends of inner surfaces of both end portions of the folding structure, and only the upper ends of the inner surfaces of the both end portions of the folding structure may be attached to each other when the folding structure is folded. A Velcro tape may be formed at the attaching portion, a male loop of the Velcro tape may be formed at one end portion of the both end portions, and a female loop of the Velcro tape may be formed at the remaining end portion.

In this way, when the folding part has a U-shape, because a narrow space may exist between surfaces forming each of the folding parts 165 and 168 while the first cover 160 is folded, when unfolding the folding structure of the first cover which was folded, a process of unfolding the folding structure can be prevented from being hindered due to the surfaces forming the folding parts being stuck to each other.

Also, like the above-mentioned C-arm head cover including the V-shaped folding parts, the C-arm head cover according to still another embodiment of the present invention may include one or three or more U-shaped folding parts, have a snap button formed at an attaching portion, and have a form keeper including an interlining cloth, a finishing material, and a durable sheet formed along an outer boundary of the first cover 160 of the C-arm head cover.

Meanwhile, in the case of the above-described C-arm head cover, although attaching portions of the folding structure may be formed only at inner surfaces of both end portions of the folding structure, attaching portions may also be formed at all surfaces of portions forming the folding structure in some cases.

Figure 10:
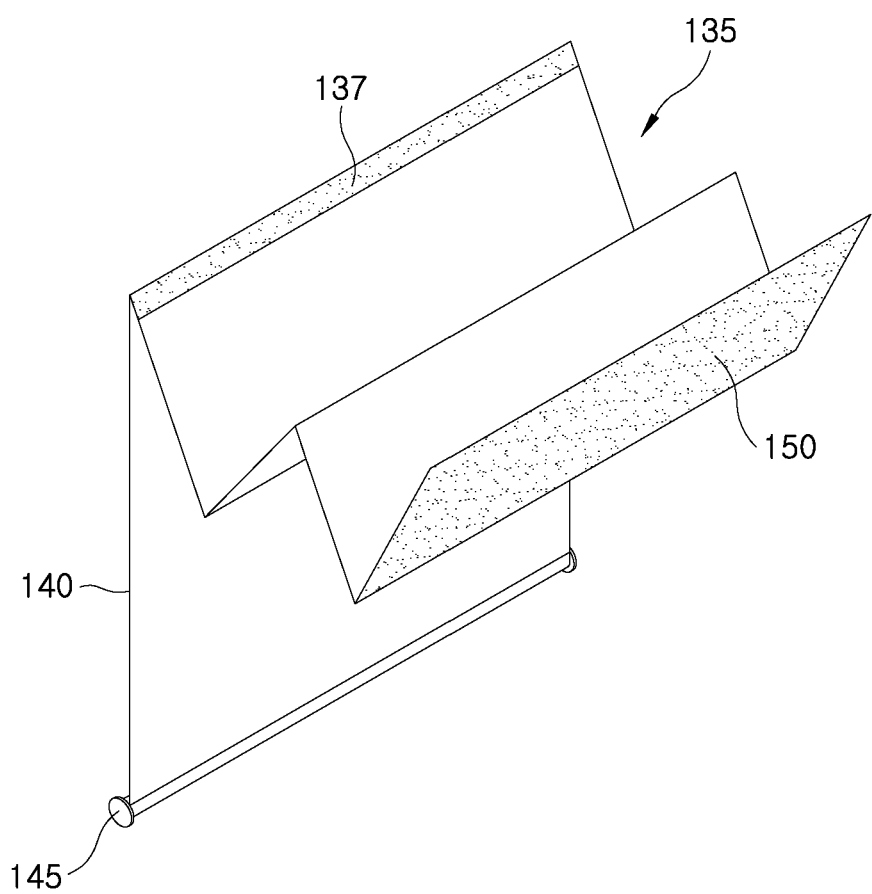
FIG. 10 is a view illustrating a C-arm head cover according to yet another embodiment of the present invention.

Hereinafter, a C-arm head cover according to yet another embodiment of the present invention will be described with reference to FIG. 10. FIG. 10 is a view illustrating a C-arm head cover according to yet another embodiment of the present invention.

Referring to FIG. 10, unlike the above-mentioned C-arm head cover according to the present invention, a C-arm head cover 130 according to yet another embodiment of the present invention has a fixing part formed in a first cover other than being independently formed from the first cover.

Specifically, a fixing part 150 of the C-arm head cover 130 according to yet another embodiment of the present invention may be formed at an outer surface of an outer boundary portion disposed at the opposite side of a second cover 140 of both boundary portions of a folding structure of a first cover 135. The fixing part 150 may have a fixer including an adhesive and enable the first cover 135, i.e., the C-arm head cover 130, to be fixed to a predetermined object such as a sterile cloth.

Because the C-arm head cover according to yet another embodiment of the present invention has the fixing part 150 formed in the first cover 135 instead of having a separate fixing part, an outer boundary surface of the first cover 135 at which the fixing part 150 is formed is attached and fixed to a sterile cloth and is substantially not used for covering the C-arm head 20. Consequently, the C-arm head cover 130 according to yet another embodiment of the present invention may be used when an area of a C-arm head cover required to cover a C-arm head is small due to a small size of a C-arm. Consequently, the C-arm head cover according to yet another embodiment of the present invention may be usefully used when a treatment space is small.

As described above, in the case of the C-arm head cover according to the present invention, because a first cover of a C-arm head is folded when a contaminated C-arm head is placed at a lower portion of a C-arm table, contamination of a folding part of the first cover is prevented. When the C-arm head moves upward from the lower portion of the C-arm table, the first cover is unfolded so that the unfolded first cover or the first cover and a second cover a contaminated C-arm head to protect a sterile cloth from the contaminated C-arm head.

In this way, by folding or unfolding a first cover according to a position of a C-arm head according to circumstances, an inconvenience of having to replace a sterile cloth every time the C-arm head is moved upward from a lower portion of a C-arm table as when a side image of the patient is captured can be prevented and radiographic imaging can be performed several times by setting a sterile cloth for one time. Therefore, radiographic imaging can be efficiently and promptly performed on a patient, and an unnecessary waste of sterile cloths can be prevented.

Embodiments of the present invention have been described above with reference to the accompanying drawings. However, one or ordinary skill in the art to which the present invention pertains should understand that the present invention may be embodied in other specific formed without changing the technical spirit or essential features thereof. Therefore, the embodiments described above should be understood as being illustrative in all aspects instead of limiting.

The invention claimed is:

1. A C-arm head cover for a radiographic imaging device having a C-arm head and a C-arm table, the C-arm head cover comprising:
   a fixing part having a fixer to be fixed to a predetermined object;
   a first cover extending from the fixing part and having a folding structure; and
   a second cover extending from the first cover and hanging downward,
   wherein, when the C-arm head moves from a lower portion to an upper portion of the C-arm table, the folding structure of the first cover is unfolded, and the first cover and the second cover or the first cover covers at least a portion of the C-arm head.

2. The C-arm head cover of claim 1, wherein the fixing part has a configuration to be fixed to a sterile cloth of a patient by the fixer.

3. The C-arm head cover of claim 1, wherein the fixer is an adhesive.

4. The C-arm head cover of claim 2, wherein a storage space is defined in the fixing part and the storage space does not overlap with a portion of the fixing part fixed to the sterile cloth.

5. The C-arm head cover of claim 1, wherein the folding structure of the first cover includes folding parts having one or more patterns in V or U shape.

6. The C-arm head cover of claim 5, wherein, when the folding structure is folded, both ends of the folding parts include attaching portions, which have configurations to be detachably attached one another.

7. The C-arm head cover of claim 6, wherein the attaching portions include a Velcro tape.

8. The C-arm head cover of claim 6, wherein the attaching portions include a snap button.

9. The C-arm head cover of claim 1, wherein a form maintenance structure is added to the first cover.

10. The C-arm head cover of claim 9, wherein the form maintenance structure includes an interlining cloth.

11. The C-arm head cover of claim 9, wherein the form maintenance structure includes a finishing material.

12. The C-arm head cover of claim 9, wherein the form maintenance structure is a durable sheet.

13. The C-arm head cover of claim 1, further comprising a weight member attached to the second cover flattening the second cover in a gravity direction.

14. A C-arm head cover for a radiographic imaging device having a C-arm head and a C-arm table, the C-arm head cover comprising:
  a first cover having a folding structure; and
  a second cover extending from the first cover and hanging downward,
  wherein a fixing part is formed at an outer surface of an outer boundary portion of the folding structure of the first cover at an opposite side from the second cover;
  the fixing part has a fixer fixed to a predetermined object; and
  when the C-arm head passes a lower portion of the C-arm table supporting the predetermined object, and the C-arm moves to an upper portion of the C-arm, the folding structure of the first cover is unfolded, and the first cover and the second cover or the first cover covers at least a part of the C-arm head.

15. The C-arm head cover of claim 14, wherein the fixing part has a configuration to be fixed to a sterile cloth of a patient by the fixer.

16. The C-arm head cover of claim 14, wherein the folding structure of the first cover includes folding parts having one or more patterns in V or U shape.

17. The C-arm head cover of claim 16, wherein, when the folding structure is folded, both ends of the folding parts include attaching portions, which have configurations to be detachably attached one another.

18. The C-arm head cover of claim 17, wherein the attaching portions include a Velcro tape.

19. The C-arm head cover of claim 14, wherein a form maintenance structure is added to the first cover.

20. The C-arm head cover of claim 14, further comprising a weight member attached to the second cover flattening the second cover in a gravity direction.

* * * * *